United States Patent [19]
Chandler

[11] Patent Number: 6,146,589
[45] Date of Patent: Nov. 14, 2000

[54] ASSAY DEVICE FOR DETECTING THE PRESENCE OF AN ANALYTE INVOLVING SEQUENTIAL DELIVERY OF REAGENTS THROUGH A LIQUID CIRCUIT

[75] Inventor: John Anthony Chandler, Cardiff, United Kingdom

[73] Assignee: British Biocell International Limited, Cardiff, United Kingdom

[21] Appl. No.: 08/875,648

[22] PCT Filed: Feb. 1, 1996

[86] PCT No.: PCT/GB96/00230

§ 371 Date: Oct. 3, 1997

§ 102(e) Date: Oct. 3, 1997

[87] PCT Pub. No.: WO96/24060

PCT Pub. Date: Aug. 8, 1996

[30] Foreign Application Priority Data

Feb. 3, 1995 [GB] United Kingdom .................... 9502112

[51] Int. Cl.[7] ..................................................... G01N 21/00
[52] U.S. Cl. ................. 422/58; 422/56; 422/57; 422/61; 422/69; 422/100; 422/103; 422/70; 422/73; 436/169; 436/170; 436/525; 436/805; 436/806
[58] Field of Search ..................................... 422/100, 103, 422/58, 61, 70, 73, 69, 56, 57; 436/169, 170, 525, 805, 806

[56] References Cited

U.S. PATENT DOCUMENTS 5,198,193  3/1993  Bunce et al. .............................. 422/100

FOREIGN PATENT DOCUMENTS

WO 91/01003  1/1991  WIPO ............................. G01N 33/53

*Primary Examiner*—James C. Housel
*Assistant Examiner*—Jennifer L. Russert
*Attorney, Agent, or Firm*—Dann, Dorfman, Herrell and Skillman

[57] ABSTRACT

An assay device for detecting the presence of an analyte in a sample, wherein a visible signal indicative of the presence or absence of said analyte is produced at a detection site on a support, characterised in that said signal is generated or enhanced by means of a signal enhancement reaction between a labelled first binding reagent which is labelled and a label developing means, which are arranged to be delivered to the detection site in a single assay step but in a sequential manner such that the first binding reagent arrives at the detection site ahead of the label developing means. The sequential delivery of the reagents to the detection site is provided by techniques such as liquidic circuits, slow release agents, and others. Methods of carrying out assays and kits for use in the assays form a further aspect of the invention.

29 Claims, 12 Drawing Sheets

ASSAY DEVICE FOR DETECTING THE PRESENCE OF AN ANALYTE INVOLVING SEQUENTIAL DELIVERY OF REAGENTS THROUGH A LIQUID CIRCUIT

The present invention relates to an analytical device, specifically an integrated one step amplified assay system which is particularly useful for sensitive rapid test diagnostic devices; as well as to assay methods and to kits for use in assays.

One step rapid test systems are being increasingly used in a very wide range of applications, for example in clinical immunoassays such as those used in testing for pregnancy, sexually transmitted diseases, food testing, bacteriological infections, allergen detection, veterinary testing, environmental control, toxins, biological agents, etc. In many other cases, however, the signals from current rapid tests are not sensitive enough to provide a qualitative or quantitative result, especially when the concentration of the substance to be detected is already extremely low in the sample, as for example in detection of HIV antibodies in saliva or blood, other viral infections or low levels of bacteria in urine or faeces which indicate the onset of a particular disease.

Preferably a one-step assay uses a simple, inexpensive, disposable device that requires little or no skill to operate. The application of sample to the device is carried out as a single step, and preferably no subsequent washes or fluid changes are required. The result is presented as a visible signal which is easily read and requires no instrumentation in order to do so.

Such rapid test devices generally include particles such as coloured latex, carbon or gold, and it is these particles which are responsible for generating the final signal. A well known example of such devices are pregnancy testing kits where levels of the hormone βHCG in urine are tested. In these devices, gold or latex conjugated to antibodies for βHCG is responsible for generating a visible signal.

Examples of known devices of this type are shown in EP-B-176799 and EP-B-291194.

In order to generate directly a visible signal, it is important that the particles responsible for generating the signal are of a certain size. In the case of gold particles, these should exceed 10 nm, and are preferably greater than 40 nm in size in order to ensure that a clear visible signal is produced. However, there are limits to the sensitivity of these rapid one step tests which restricts their usefulness.

There is a requirement for rapid diagnostic tests which are ever more sensitive in order to detect analytes which are in very low quantities. Non-invasive sampling is frequently preferred although the concentrations of analytes in saliva are typically one hundred times lower than those found in blood.

The present invention provides a rapid detection device which is highly sensitive.

According to the present invention there is provided an assay device for detecting the presence of an analyte in a sample, wherein a visible signal indicative of the presence or absence of said analyte is produced at a detection site on a support, characterised in that The device is a strip device having a single channel said signal is generated or enhanced by means of a signal enhancement reaction between a first binding reagent which is labelled and a label developing means, which first binding reagent and label developing means are arranged to be delivered to the detection site in a single assay step but in a sequential manner such that the first binding reagent arrives at the detection site ahead of the label developing means.

In particular, the invention provides an assay device comprising (a) a porous element;
(b) a first binding reagent which specifically binds an analyte, is movable through the porous element under the influence of a liquid into a detection zone, and comprises an invisible label;
(c) a second binding reagent which specifically binds either said analyte in a manner which is complementary to that of the first binding reagent or which competes with said analyte for binding to said first binding reagent and is immobilised within said detection site, and
(d) label developing means which is movable under the influence of a liquid into said detection site after said first binding reagent, said label developing means being able to render the invisible label visible. The assay device just-described is a strip device having a single channel and the first binding reagent and the labelled developing means are arranged to be delivered to the detection zone in a single step by application of the sample.

As used herein the term 'invisible label' refers to labels which are not generally visible or only poorly visible to the naked eye, even when concentrated in a capture zone or detection site in an assay situation. Examples of such labels include enzyme labels or particulate labels which are either not collected in sufficient quantity to provide a good visible signal, or are of particularly small size, for instance less that 10 nm in size, suitably less than 5 nm in size, and preferably from 1–2 nm.

The label developing means comprises a reagent which is able to develop the invisible label to render it visible, thereby generating a signal. The nature of the developing means will depend upon the nature of the invisible label used.

For example, when the invisible label is an enzyme label, the label developing means may comprise diaminobenzidine or other known enzyme developing agents.

When the label comprises a particulate label, the developing means may deposit material onto the particles to render them visible. Suitable particulate labels include metal labels which are capable of being enhanced such as gold, silver, selenium or platinum labels or particulate latex labels if they are coated with a substance capable of being enhanced such as enzymes or metal coatings. Preferably the particulate label comprises a particulate metal label and most preferable a particulate gold label.

When a particulate metal label is used, a suitable developing means will comprise a silver reagent, such as silver lactate together with a suitable developer such as hydroquinone, for example as described by Holgate et al., J. Hisotchem. Cytochem. 31, 938–944. The silver reagent is suitably maintained in the appropriate zone of the porous member in dry form where it will remain until resuspended by liquid passing through that zone towards the detection site.

Silver enhancing reagents are available commercially for example from British Biocell International Ltd., of Golden Gate, Ty Glas Avenue, Cardiff, UK.

Use of a particulate gold label combined with a silver enhancing system can mean that the signal intensity is increased by as many as 100–1000× making the analytical test device of the invention viable for a much wider range of applications than have hitherto been possible. The speed of the signal development will depend upon the formulation of the silver solution and on the size of the gold particles as well as the geometric arrangement of the device. Although the particles may be in the size range of for example from 1–100 nm, they are preferably small particles of less than 5 nm. An advantage of the use of small particles is that, for a given sample, a far greater number of these particles can be accumulated in the detection zone for subsequent enhancement, due to a reduced steric requirement. This provides a greatly increases signal compared to unenhanced larger particles.

Where such an assay is formulated as a one step process, it is necessary to ensure that sample suspected of containing analyte as well as labelled first binding reagent reaches the detection site in advance of the label developing means. Such an arrangement may take a number of physical forms and one such arrangement comprises a liquidic circuit as described for example in GB Patent Application No. 2231150A. The use of liquidic circuits for supplying label developing means to a preformed signal in a one step assay has not been disclosed hitherto.

Using this technology, channels of differing length and or width are created for the liquid moving through different zones by means of a series of substantially impermeable barriers. One particular form of liquidic circuit, the printed liquidic circuit, comprises one or more layers of filter paper or membrane onto which is printed a wax pattern which creates the substantially impermeable barriers. The reagents required in the assay may be dried onto the device at the appropriate positions. Channel length and configuration are used to control the time of arrival of liquid at various parts of the circuit, in particular in the present case, the detection site. Channel width is used to control the liquid pressure.

The zones are arranged so that a liquid sample suspected of containing analyte and the first binding agent reach the detection site before the label developing means. If the liquid sample suspected of containing analyte is applied separately from the first binding reagent, the zone through which it travels must be arranged so that any analyte arrives at the detection site prior to the first binding reagent in order to ensure that an accurate signal is generated.

Hence, one embodiment of the invention is an analytical test device comprising:

(a) a porous element divided into a plurality of zones which are substantially impermeable to each other but which intersect at a detection site;

(b) a first binding reagent which specifically binds an analyte, said binding reagent being located in one zone and movable through the porous element under the influence of a liquid into said detection site, said first binding reagent comprising an invisible label;

(c) a second binding reagent which specifically binds either said analyte in a manner which is complementary to that of the first binding reagent or which competes with said analyte for binding to said first binding reagent and is immobilised within said detection site, and (d) label developing means located in zone other than said one zone and movable under the influence of a liquid into said detection site, said label developing means being able to render the invisible label visible.

Suitably the first binding reagent and the label developing means will each be moveable towards the detection site under the influence of liquid travelling along the porous element. In addition, a liquid suspected of containing analyte will be moveable towards the detection site, either in combination with the first binding reagent or along a further zone provided in the device for this purpose. Different liquids may also be applied to each zone or group of zones and these can be applied individually to a sampling region or sampling well arranged in each zone.

However, in a preferred embodiment, the device is arranged such that at least the first binding reagent and the label developing means are moved towards the detection site under the influence of the same liquid which will comprise the sample under test. This gives rise to one-step rapid assay systems.

The zones or groups of zones are suitably arranged in the device so that the same sample can be applied simultaneously to the sampling region of all or a group of zones from where it travels through the porous member to the detection site. For instance, the zones may be arranged in substantially adjacent parallel relation although the arrangement of impermeable barriers in any one zone may define a longer liquid path than in the other.

This allows the analytical test device to be employed as a rapid assay one step system since the sample will carry both the first binding reagent and the label developing means to the detection site.

However other methods may be employed in order to ensure sequential delivery of the first binding reagent and the labelling means to the detection zone. These include the use of slow release compositions which ensure that the label developing means is released later than the first labelled binding reagent.

Such releasing agents may include gelatin and other proteins, polyethylene glycol(PEG), polyvinylpyrollidine (PVP) and other polymers, surfactants, gum arabic, sucrose and other sugars, clays, oils, lipids, resins, salts and other slow release agents such as are used in the pharmaceutical industry. Such slow release reagents may be applied typically in concentrations of 0.1–5%, preferably in the order of 1%w/v.

Other means of controlling the release of the reagents from the membrane to allow flow towards the detection zone include methods for altering the hydrophobicity of the membrane in those zones such that wetting of the zones by the sample may be controlled. Such methods includ the use of certain hydrophobic surfactants such as Triton X 705, high salt concentrations (e.g.5% NaCl), certain fatty acids or polyamino acids such as poly L tryphophan (Sigma), all having high hydrophobic properties and capable of being impregnated into the membrane.

Alternatively the mobile labelled binding reagents and label developing means may be enclosed within or behind semipermeable barriers such as gelatin, glycerol, polymers, etc, such that they may be released sequentially as the sample penetrates these barriers to resolubilise the reagents. The choice of barrier material will in this way govern the rate of solubilisation and release of the reagents for movement towards the capture zone.

In a further embodiment, the mobile labelled binding reagent and/or the label developing means is applied on a separate layer of porous material which contacts the porous element in such a way that liquid travelling through the porous element first passes under the separate porous layer, and as more liquid flows, gradually this is absorbed into the porous layer, Ultimately the liquid will flow through the device, collecting the first binding reagent or label developing means applied there. The further porous layer may comprise membranes, paper or glass fiber pads as appropriate.

In yet a further embodiment, the labelled first binding reagent and the label developing means are arranged on the porous element in such a way that the labelled first binding reagent is able to proceed directly toward the detection zone with the laminar flow of the liquid sample whereas the label developing means does not encounter the detection zone. However if a suitable barrier is placed in the path of the developing means, it may be diverted towards the detection zone, although the diversion process will necessarily delay the progress of the liquid. The barrier may be positioned in the path of liquid carrying the label developing means ab initio, but preferably the label developing means itself contributes to the production of the barrier so that a slightly longer delay between the arrival of the labelled first binding reagent and the label developing means takes place.

This embodiment is most appropriate where the label is a particulate metal such as gold, and the developing means is one which causes a deposit of material on the surface of the metal particle, such as a silver reagent. For example, small metal particles are arranged immobilised on the porous element in the path of the label developing means in such a way that if expanded, they form a barrier which will direct the label developing means toward the detection zone (as illustrated hereinafter). In use, the label developing means encounters these particles first and forms deposits on them. As the deposit builds up, the enlarged particles form a barrier to continued laminar flow of the liquid containing the label developing means which is thereby diverted.

This principle may be used in a broad range of assays where diversion of liquid in the course of the assay to give rise for instance to sequential reactions or reaction steps is required. It is not necessary that the label developing means is required to enhance any signal produced although clearly it would simplify matters, if these two functions were required, that they were combined in a single label developing means.

Assay devices employing this principle form a further aspect of the invention.

The devices of invention may be adapted for 'sandwich' or 'competitive' assay strategies. In a sandwich assay, the second binding reagent binds to said analyte in a manner which is complementary to the first binding reagent. In this case, the first binding reagent moves into the detection zone under the influence of the liquid sample suspected of containing the analyte. Any which has bound to analyte will accumulate in the detection site there before the label developing means reaches it, whereupon a visible signal will be produced.

In a competitive assay, the second binding agent competes with the analyte for binding to the first binding reagent. Once again, the first binding reagent is moved into the detection zone under the influence of a liquid sample under test but in this instance, any which has bound to analyte will not be retained in the detection site. Only unbound first binding reagent will be accumulated there and give rise to the visible signal. In this instance, the greater the signal, the less analyte is present in the sample.

In this type of assay a further binding agent which specifically binds the first binding reagent or the analyte in a manner which is complementary to the first binding reagent may also be provided. This further binding agent is immobilised at a catch site which is located beyond the detection site along the sample path. This further binding agent will accumulate bound analyte/first binding reagent complexes or conjugates in the catch site, whereupon a visible signal is generated upon the arrival of the signal developing means. In this way, the signal generated by bound as compared to unbound first binding reagent may be compared in order to provide a more qualitative assessment of the amount of analyte present in the sample under test.

If necessary or desired, filtration means may be provided in the devices of the invention, for example in some of the zones of devices which include impermeable barriers, or simply in front of reagents applied to the surface of a membrane in the direction of sample liquid flow, in order to remove unwanted elements from the sample in such zones or areas. These filtration means may comprise physical filters or immunological or biochemical binding agents which bind the unwanted elements. For example, when a serological assay is performed on a serum sample, the presence of the full range of serum antibodies may give rise to a series of false positives if the serum is used for example as a carrier liquid for the first binding reagent of the label developing means or even as a wash liquid as described below. In such a case, these may be removed from the serum in the relevant zones by providing a immunological barrier for example comprising anti IgG antibodies such as anti-human IgG antibodies which are immobilised on the porous member in such a way as to ensure that serum passes through this barrier before reaching the detection site.

The use of such filtration means in assays forms a further aspect of the invention.

The use of technology such as the liquidic circuit technology will allow additional steps to be incorporated into the assay. For instance, one or more additional zones may be provided and arranged to deliver a wash liquid to the detection site. For example delivery of a wash liquid may be desirable after the first binding reagent but prior to the arrival of the label developing means. This will have the effect of washing the detection site free of any labelled first binding reagent which is not bound there before the signal is produced. The wash liquid may comprise the sample itself which is optionally filtered during its passage through its associated zone in order to remove contamination and excess reagents.

Additional washing steps may be particularly appropriate in the case of serological assays for example of blood samples, in order to remove excess serum and non-specific antibodies from the detection site.

Similarly label development resulting in signal production may be terminated if appropriate by providing a further zone which is arranged to deliver liquid, once again preferably originating from the sample itself, to the detection site as a final step.

The devices of the invention can be arranged so that a series of reactions are effected sequentially and separated in time depending for example, in the case of liquidic curcuits upon the length of liquid channels defined within each liquid impermeable zone of the porous member, or on the nature of the slow release or barriers presented to the various reagents.

In a preferred embodiment, wicks or wicking zones can be provided into which liquid and excess reagents are channelled both before and after they have taken part in the reactions. This improves the liquid flow through the device.

The selection of the first binding reagent and the second binding reagent in any particular case will depend upon the nature of the analyte under test. When the analyte comprises an antigenic protein or polypeptide, such as a hormone like βHCG, the first and second binding reagents may comprise antibodies or antibody binding fragments which are specific for those proteins, as are conventional in the art, particularly in relation to sandwich assay or competitive assay techniques. Alternatively, the device of the invention may be adapted for use with serological assays where the analyte may itself comprise a specific antibody such as HIV antibodies. In such a case, the second binding reagent suitably comprises an antigen to which the target antibody specifically binds and the first binding agent comprises an anti-antibody which binds the analyte antibody. In such a case, the analyte antibody is suitably immobilised at the detection site prior to the introduction of the labelled anti-antibody which is applied such that it arrives at the detection zone at a somewhat later time, for example by administration to a different zone of a liquidic circuit.

Additionally the analyte may comprise a nucleic acid such as an RNA or DNA. In such a case, the first and second binding reagents may comprise nucleic acid binding components such as labelled nucleic acid probes which hybridise with the nucleic acid under test.

Suitable porous elements for use in the device include porous membranes and papers as are well known in the art. They include nitrocellulose membranes.

The device may comprise a simple dipstick. Depending upon the geometry of the device, this may be somewhat wider than the usual dipstick mounted on a plastic backing with no protection applied to the surface. Alternatively, the device may be encapsulated within an enclosure such as a plastic housing which is provided with an aperture for application of the sample. Alternatively, it may take the form of a laminated card where the sample end is exposed by cutting or tearing the laminate immediately before use and then immersing in the sample. Yet another form may be a flat card on which all the chemistry, barriers and circuits are mounted and the card is covered with an impervious membrane, for example a plastic membrane which is spray applied.

The invention will now be particularly described by way of example with reference to the accompanying diagrammatic drawings in which.

Figure 12:
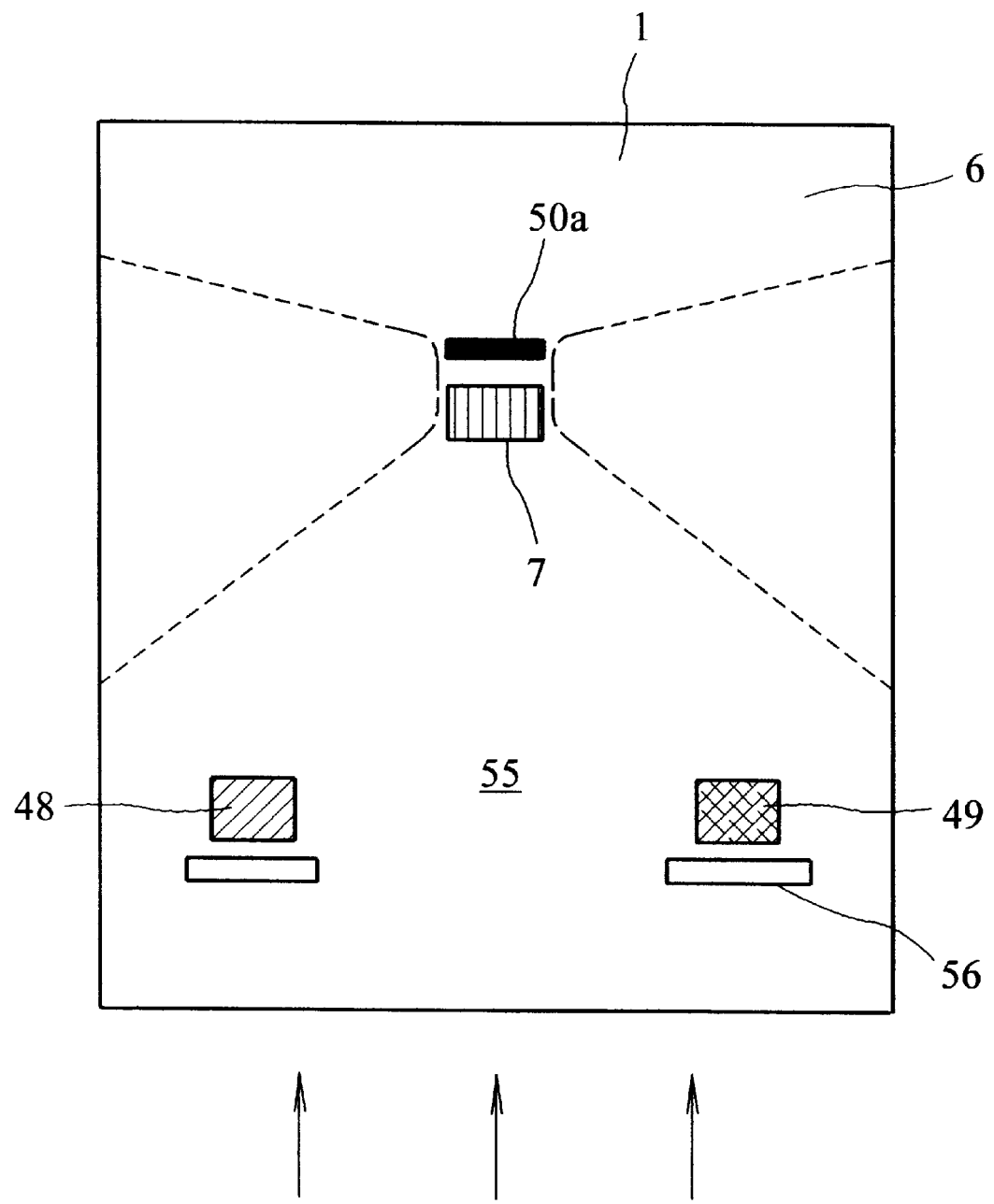

FIGS. 10A and B are front and side respectively schematic drawings illustrating an analytical test device with sequential release and linear flow of reagents from the surface of the membrane for subsequent signal enhancement in a sandwich assay;

FIGS. 11A and B are front and side respectively schematic drawings illustrating an analytical test device with sequential release of reagents from the surface of a membrane and from a superimposed pad for subsequent signal enhancement in a sandwich assay;

FIG. 12 is a schematic drawing illustrating an analytical test device with reagents deposited behind slowly soluble barriers for gradual release and flow in a sequential manner with signal enhancement in a sandwich assay; and FIG. 13A shows a schematic drawing illustrating an analytical text device with sequential release of reagents from a superimposed or overlapping lower wick onto a membrane carrying an immobilised target binding protein for subsequent enhancement in a sandwich assay and FIG. 13B shows a side view of the same device.

Figure 1:
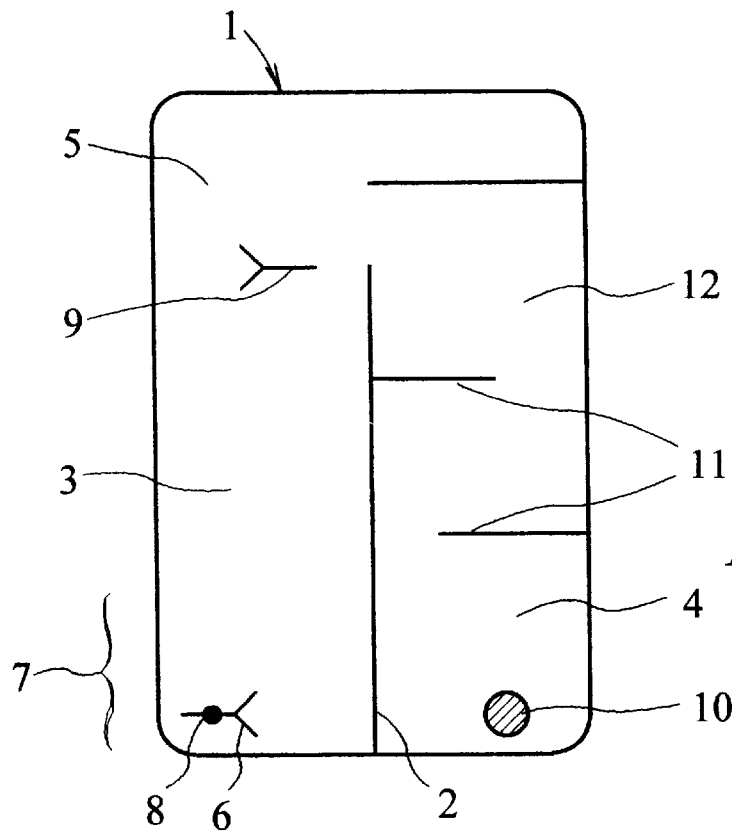
FIG. 1 is a schematic drawing illustrating the arrangement of an analytical test device before use.

The test device (FIG. 1) comprises a porous membrane (1) which is divided by means of an impermeable barrier (2) into a first zone (3) and a second zone (4) which intersect at capture site (5).

An antibody (6) for an analyte is provided within one end portion (7) of the first zone. The antibody (6) is conjugated to a gold particle (8) which is less than 5 nm in size. A capture antibody (9) which also binds the analyte is immobilised on the porous membrane (1) in the capture site (5).

A dried silver reagent (10) such as silver lactate, and developer such as hydroquinone is provided in the end portion (7) of the second zone (4). A series of impermeable barriers (11) are provided in the second zone (4) which define a channel (12).

Figure 2:
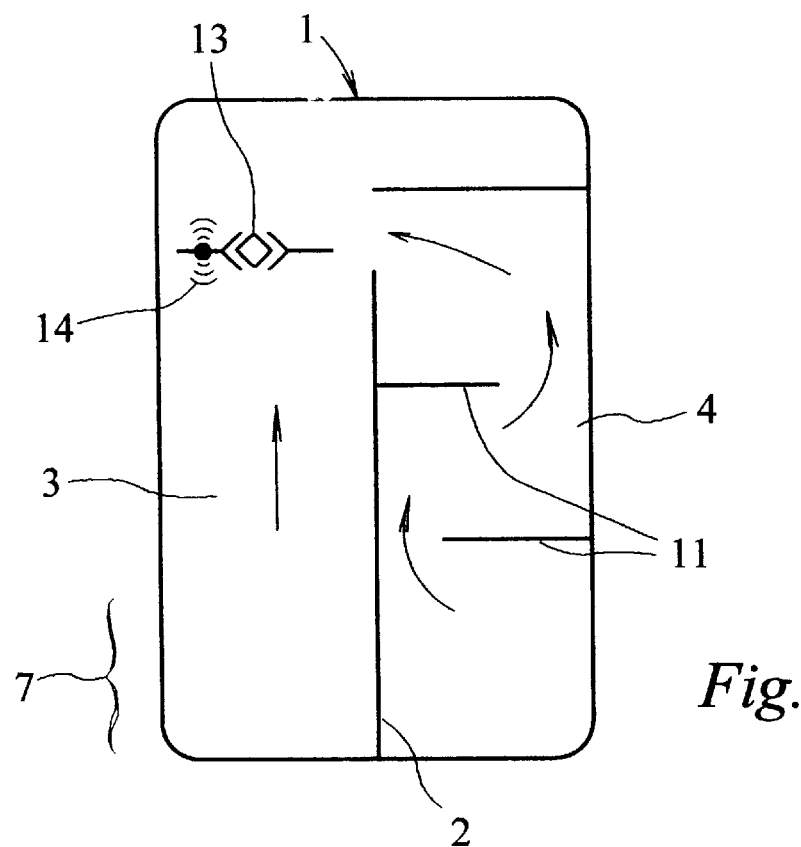
FIG. 2 is a schematic drawing showing the device of FIG. 1 at the end of an assay.

In use, the end portion (7) is immersed in a liquid sample which is suspected of containing analyte. The sample passes through the porous membrane (1). Sample which passes through the first zone (3) collects the labelled antibody (6) and carries it to the capture site (5). If analyte (13) (FIG. 2) is present in the sample it will bind to the antibody (6). Once in the capture site (5), the analyte-antibody complex will bind to the capture antibody (9).

Sample which passes through the second zone (4) will collect the silver reagent (10) and then pass through the channel (12) in the direction of the arrows. It will therefore take longer to reach the capture site (5). When it arrives, the capture site (5) will, if analyte is present, contain a concentration of gold label particles. The silver reagent (10) will react with these particles developing a brown-black visible signal (14).

Figure 3:
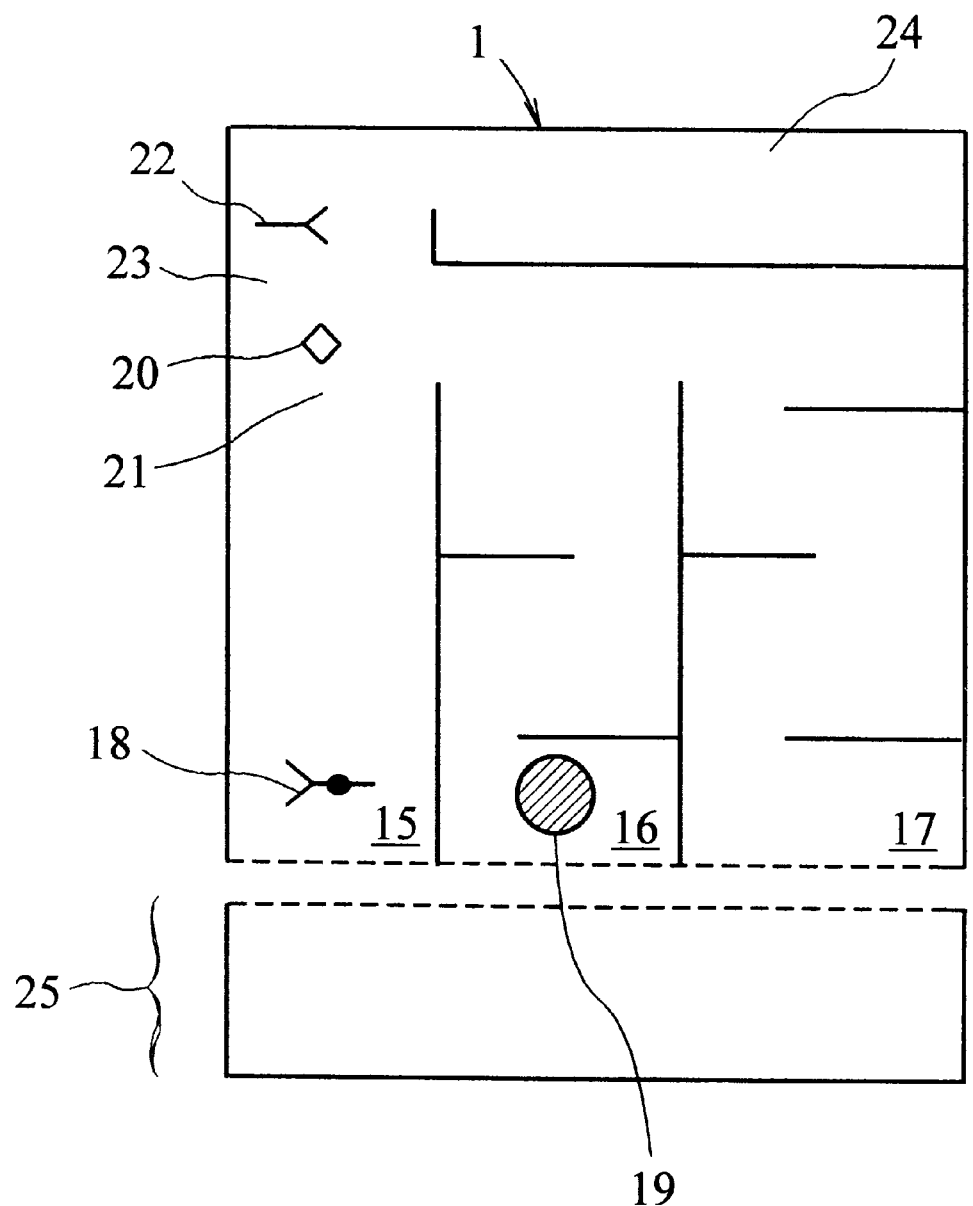
FIG. 3 is a schematic drawing illustrating the arrangement of an analytical test device which utilises a competitive assay.

In the alternative device of FIG. 3, a competitive assay can be carried out. This embodiment comprises a porous card (1) on which are defined three channels (15, 16 and 17), the first of which (15) contains a gold labelled antibody (18) such as a mouse antibody, and the second contains a silver lactate/hydroquinone combination (19). An antigen (20) which competes with the analyte for binding to the antibody (18) is immobilised at the detection site (21). An anti-antibody (22) such as an anti-mouse antibody is immobilised at a capture site (23).

Channels 15, 16 and 17 are arranged so that liquid moving along them reaches detection site (21) and capture site (23) sequentially. A wicking zone (24) is arranged to receive liquid once it has passed the capture site (23).

In use, the lower end (25) of the card (1) is immersed into a liquid sample suspected of containing analyte so that it flows through the channels (15, 16, 17). Any analyte in the sample in the shortest channel (15) binds with the gold labelled antibody (18) and then travels along the channel to encounter the immobilised antigen (20) at the detection site (21). Labelled antibody (18) which has bound to analyte will pass through this region whereas previously unbound labelled antibody (18) will be accumulated there.

Bound labelled antibody (18) which passes the detection site (21) will encounter the anti-antibody (22) and therefore accumulate in the capture site (23).

The sample travelling in the second longest channel (16) then propels the silver/hydroquinone reagent (19) into both the detection site (21) and the capture site (23) where it encounters any gold labelled antibody (18) accumulated in those sites. The gold label is enhanced to produce visible brown-black signals whose intensity is dependent upon the amount of antibody (18) present at those sites.

Finally sample travelling in the third channel (17) arrives in the detection site (21) and capture site (23) and washes the silver enhanced gold conjugate complexes there. All excess liquids are wicked into the wicking region (24).

Figure 4:
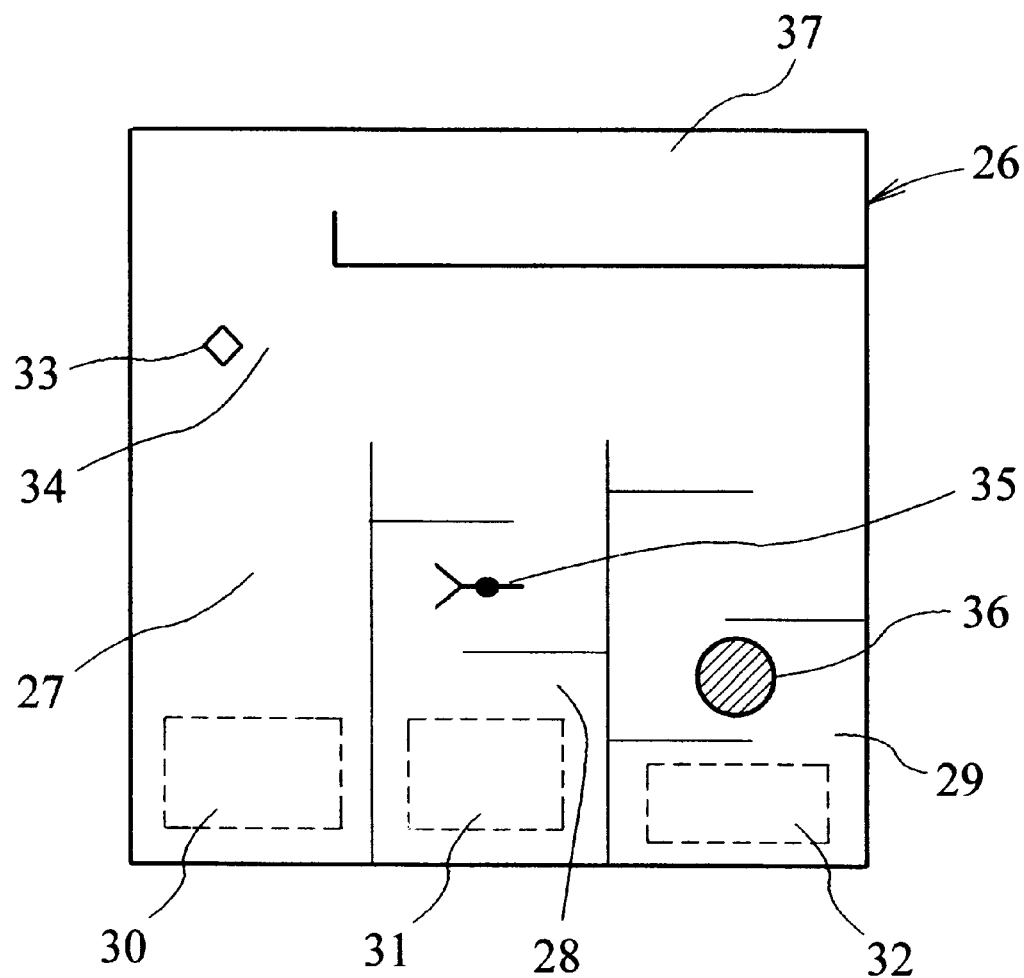
FIG. 4 is a schematic drawing illustrating an analytical test assay specifically adapted for a serological assay and incorporating wash steps.

FIG. 4 shows a further embodiment of the assay device of the invention which is specifically adapted for a serological immunoassay for the detection of serum antibodies. This device comprises a porous support (26) on which are defined first, second and third channels (27, 28, 29) of progressively longer length, each of which is provided with a liquid receiving aperture (30, 31 and 32) at an end region thereof.

Antigen (33) to which the serum antibody or analyte binds is immobilised in a detection zone (34). A gold labelled anti-antibody (35) is provided in the second channel (28) and the silver/hydroquinone developing reagent (36) is dried into the third channel (29). In use, serum sample is introduced into the aperture (30) in the first channel (27) and wash solution is placed into the other apertures (31, 32). The sample travels along the first channel 27 and encounters antigen (33) to which specific sample antibodies bind. Non-specific antibodies in the sample progress into a wicking region (37).

Meanwhile wash solution from the aperture (31) in the second channel (28) propels the gold labelled antibody (35) to the detection site (34) where it encounters and binds with any serum antibody immobilised there. Silver/hydroquinone (36) arriving later and propelled by wash liquid from the aperture (32) in the third channel (29), enhances any bound gold conjugate giving a visible signal indicative of the presence of the serum antibody in the sample.

Figure 5:
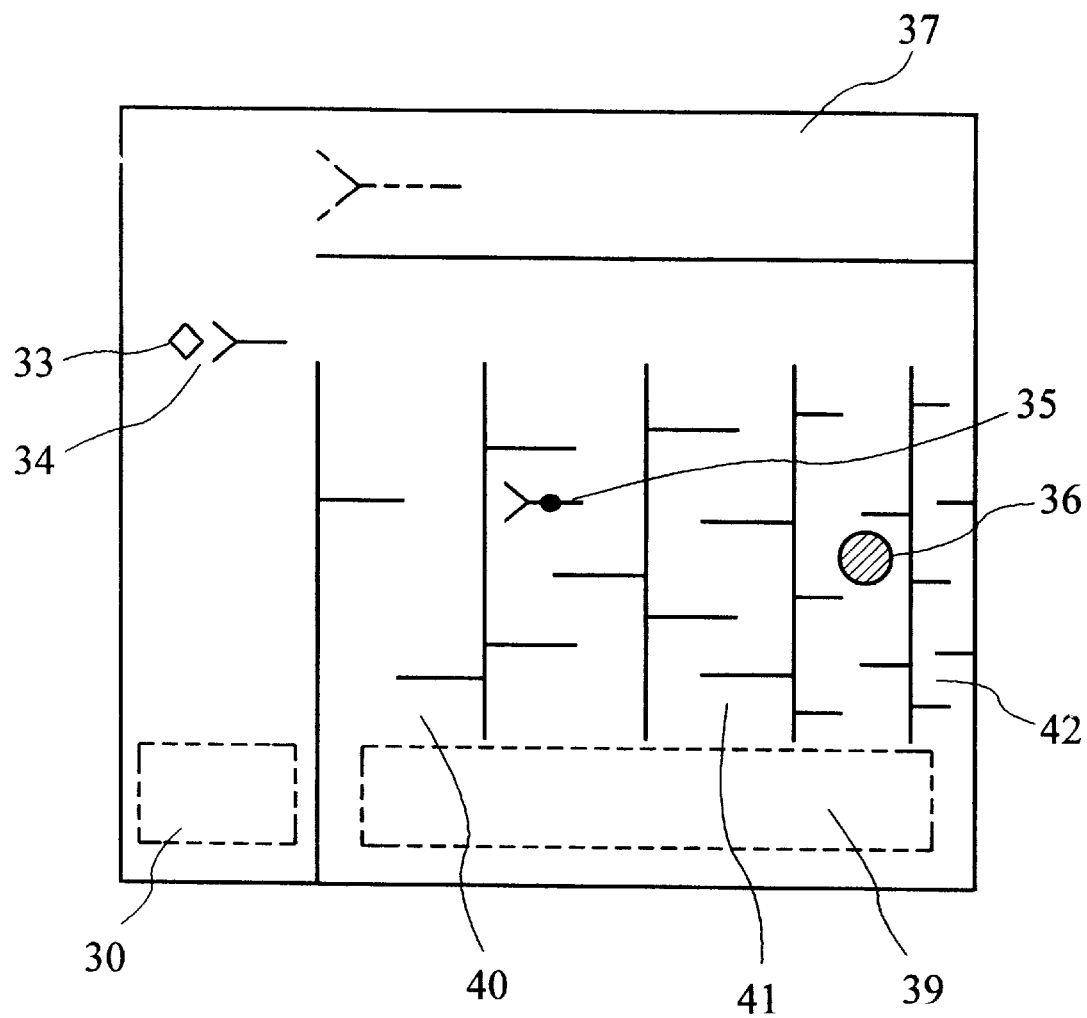
FIG. 5 is a schematic drawing illustrating a further embodiment of a test device for use in a serological assay.

FIG. 5 illustrates a modified form of the assay device of FIG. 4 which incorporates washing steps intermediate between each of the assay binding reactions and at the end of the assay. This is achieved by introducing additional channels (40, 41, 42), all of which are arranged to receive wash solution placed in a reservoir area (39). The channels (40, 41, 42) are arranged to deliver wash liquid to the detection site (34) in order respectively to (a) wash antigen/serum antibody complex formed at the site prior to arrival of the gold labelled antibody (35), (b) wash antigen/serum antibody/gold labelled antibody prior to arrival of silver/hydroquinone developing agent and (c) wash silver enhance complex at the detection site (34) and thus to terminate the enhancement.

Figure 6:
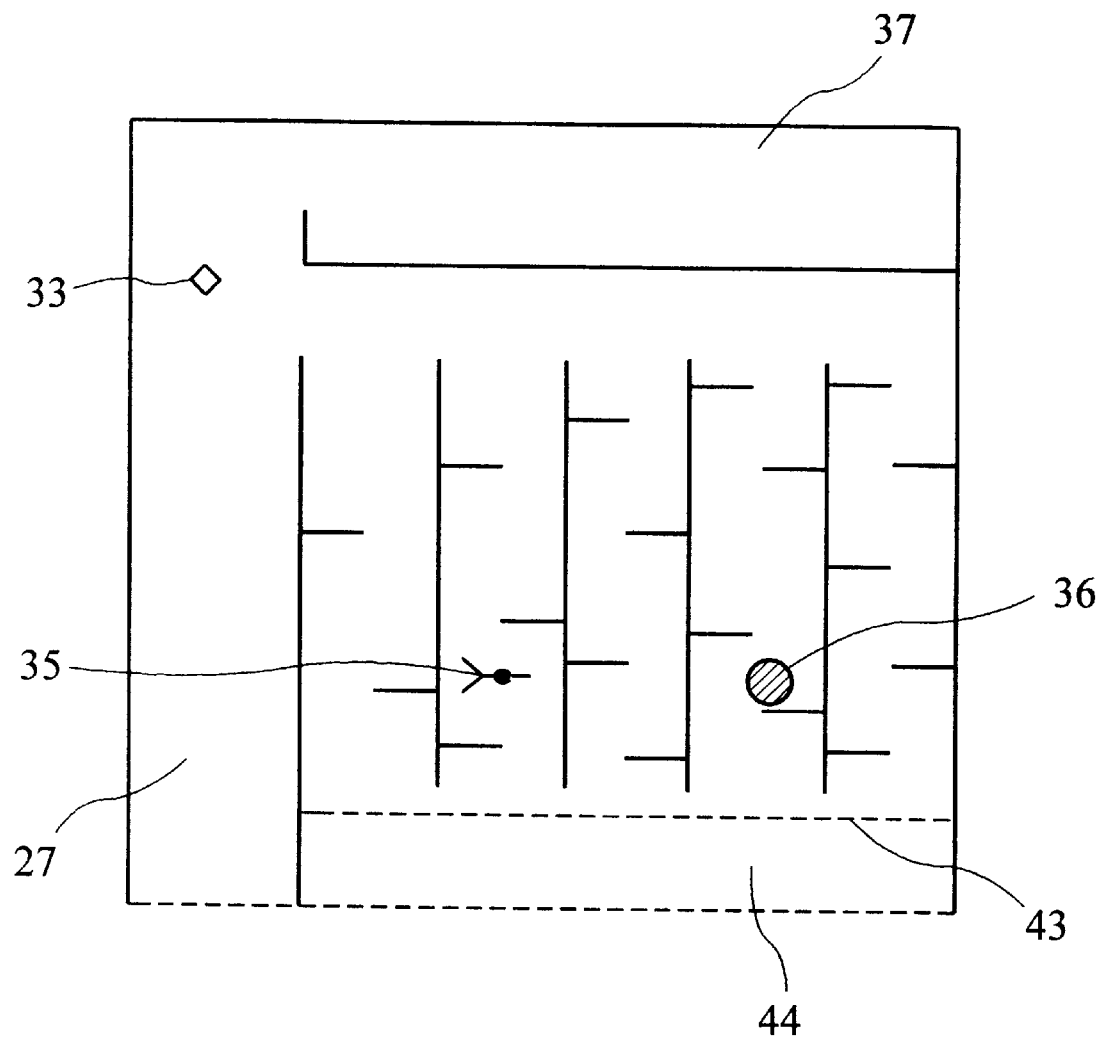
FIG. 6 is a schematic drawing of a test device adapted for use in connection with a serological assay which utilises the serological sample as a transport medium.

This embodiment may be modified as shown in FIG. 6 in order to allow for the serum sample to supply the wash steps if required. In this case, it is necessary to ensure that all serum other than that travelling in the first channel (27) contacts immobilised anti-human IgG in order to filter out serum antibodies allowing the remaining serum to act as a wash liquid. The immobilised anti-human IgG (43) is suitably provided in the form of a transverse barrier extending across each of the relevant channels. This eliminates the need to provide a separate reservoir for wash liquid.

Figure 7:
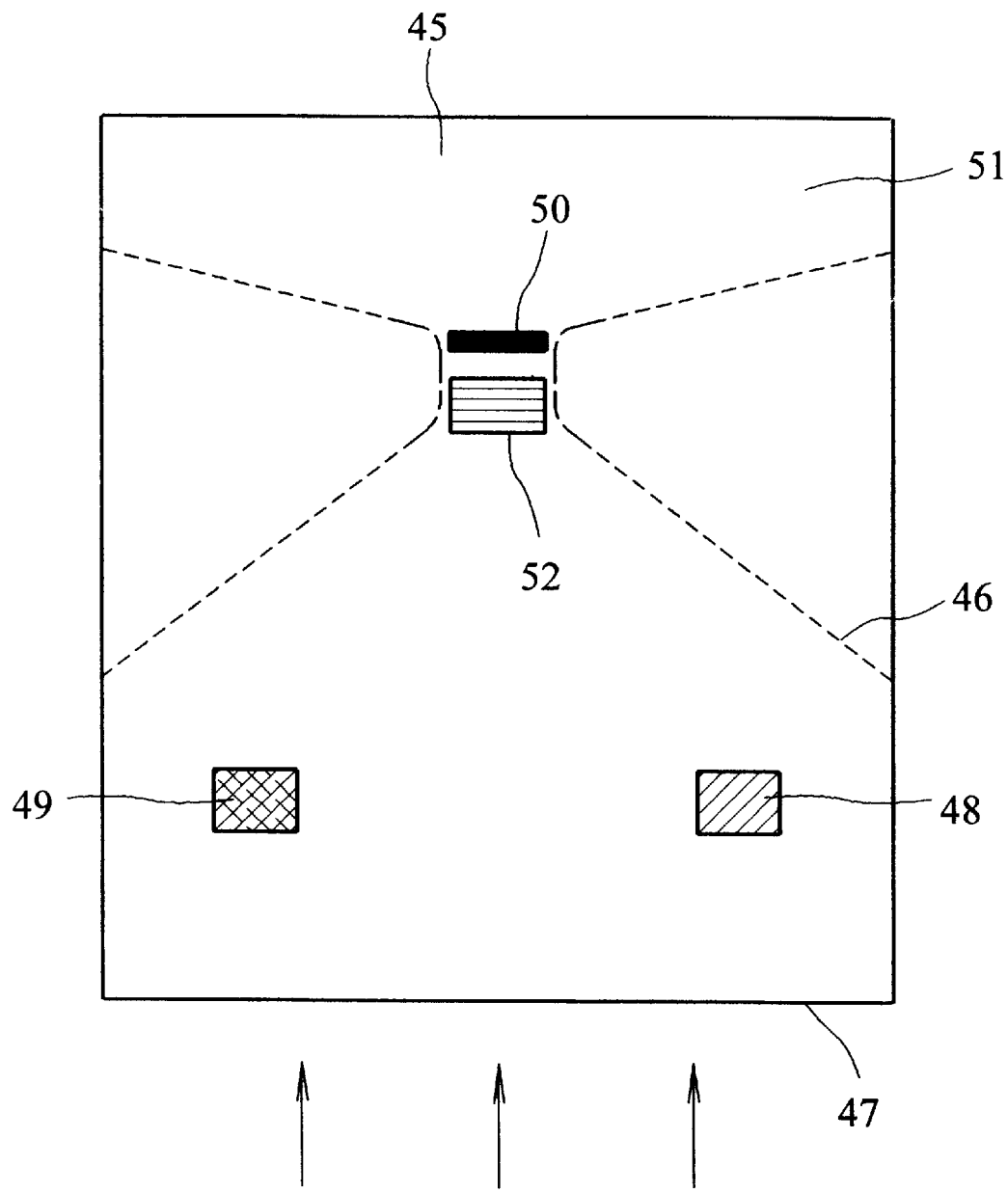
FIG. 7 is a schematic drawing illustrating an analytical test device with sequential release and controlled diffusion of reagents for a one step sandwich assay with signal enhancement.

In an alternative embodiment, the device may consist of a membrane loaded with appropriate reagents which are positioned in such a way that under the influence of the applied sample they move towards a detection zone sequentially. One such embodiment is illustrated in FIG. 7. A solid phase carrier (45), such as the previously described membranes of paper, nitrocellulose, glass fibre or other porous material is suitably coated with reagents in such a way that some remain mobile while others are immobile. The device may be suitably shaped or coated with an impermeable barrier as shown by the broken line (46) of FIG. 7 to cause a funnelling of the reagents flowing towards the detection zone.

The sample may be applied to a lower edge (47) or alternatively to a number of apertures at the lower portion of the carrier in such a way that the sample moves by capillary action towards a mobile labelled binding reagent (48) such as a gold labelled antibody and the lable developing means or mobile enhancing reagent (49) such as a silver enhancing reagents. The sample travels along the carrier (45), passing over both the mobile labelled binding reagent (48) and the mobile enhancing reagent (49), moving directly towards the immobilised binding agent (50) such as a capture antibody in a detection zone. In order to arrange a suitable sequence of events the mobile reagents (48) and (49) may be deposited on the carrier in different releasing agents to allow different release times from the carrier. By selection of appropriate releasing agents it is possible to govern the order and speed of release of the labelled reagent (48) and the enhancing reagent (49) as well as controlling the environment in which they are temporarily immobilised and subsequently reacted.

The reagents thus move sequentially in the direction of the arrow towards the detection zone and, preferably through it, being drawn by capillary action into an upper zone (51). To aid the proper interaction and uniform exposure of the binding reagent (50) with the mobile reagents (48) and (49), diffusion means (52) may be provided and positioned just before the detection zone in the path of the sample. This may take the form of an immobilised substance such as a protein (eg bovine serum albumin or BSA), polymer (eg polyvinylalcohol (PVA), PEG, PVP, etc), salt or other suitable substance such as glycerol, gum arabic, lipid which is deposited on the membrane such that it causes the reagents to be dispersed for even flow through the detection zone. The membrane may also be impregnated with a textured pattern of permeable or impermeable materials to cause such mixing or diffusion to occur at the diffusion zone. Such an impermeable material may include wax deposited on the membrane using a high resolution hot wax printer and driven from a graphics computer programme to generate the required pattern. A suitable hot wax printer is the Phaser 340 available from Tetronix Europe, UK. A suitable graphics design package is Autosketch available from Autodesk Inc, USA. Alternatively the diffusion may be achieved by placement of a separate material such as a glass fibre pad on the surface of this membrane in the diffusion zone.

Analyte present in the sample reacts first with the first labelled reagent (48) and then proceeds to move on through the detection zone. It may form a sandwich by interaction of the analyte with the binding reagent (50). Because the label on the first binding reagent (48) is not visible (eg an enzyme or small gold or other metal particle or unenhanced label) no direct signal will be detected. Subsequent movement of the sample through the detection zone will create a washing effect following this sandwich formation. The subsequent release of the enhancing reagent (49) will allow it to move towards and through the detection zone and thus produce the required signal enhancement to give an indirect signal. Further movement of the sample behind this enhancement will wash the membrane to allow a clear signal above background in the capture zone.

Figure 8:
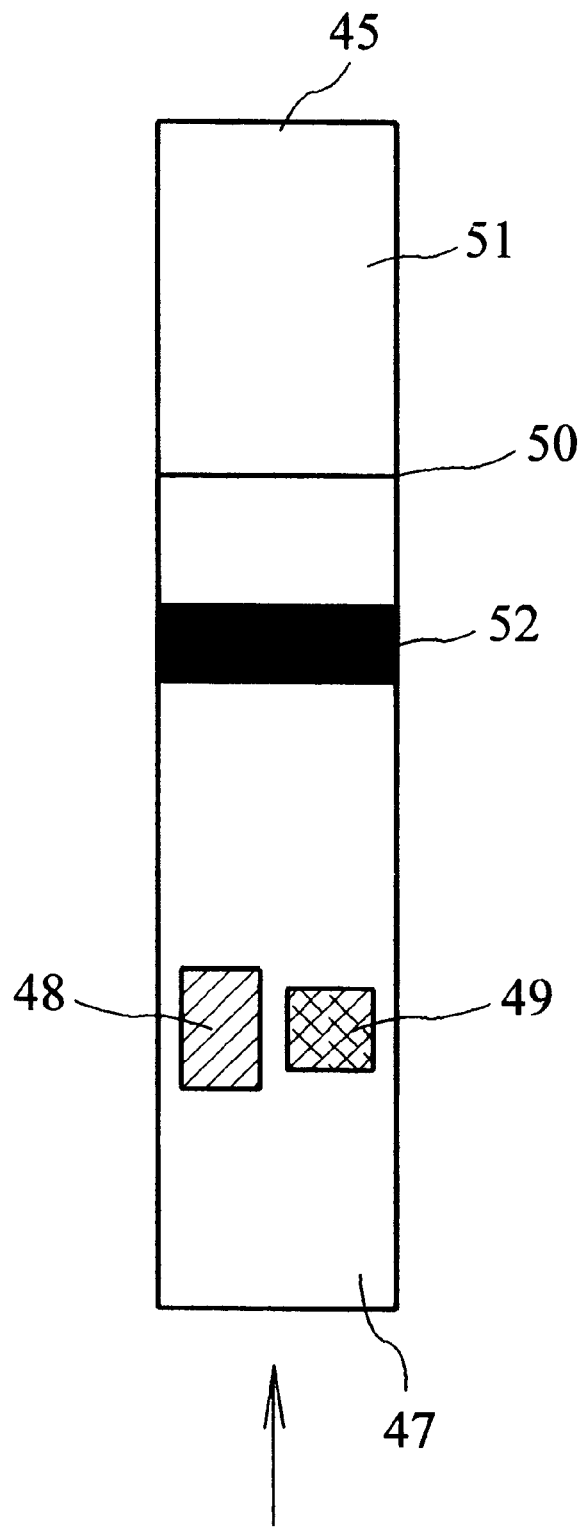
FIG. 8 is a schematic drawing illustrating an analytical test device similar to FIG. 7 but with a diffusion zone in place of funnelling.

Alternatively the device may take the form of a single narrow strip of membrane as shown in FIG. 8 whereby the mobile reagents (48) and (49) are placed in close parallel proximity at the lower part of the strip. With the use of suitable slow release agents each reagent may be caused to move sequentially towards the binding agent (50) in the detection zone, diffusion of the reagents occurring before reaching the detection zone by positioning of the diffusion means (52) immediately before the detection zone. In this way laminar flow will ensure that the reagents do not mix until they sequentially reach the diffusion means.

It was surprisingly found that as silver enhancing reagents caused the deposit of silver metal on gold labelled binding proteins within the detection zone, so the silver formed a semi permeable barrier to further flow of silver enhancing reagents through this zone. This created the effect of changing the flow path of the reagents through the detection zone, effectively allowing the final reaction product to alter the geometry of the device. This resulted in the whole of the capture zone being evenly diffused with silver ions to allow an even enhancement of the gold particles within the detection zone. In this way the laminar flow of the reagents passing through the detection zone was automatically diffused over the whole zone.

In further trials it was found that by depositing gold particles permanently on the membrane at appropriate places, the silver enhancing reagents caused the build up of silver metal which effectively changed the flow of the liquid passing through the membrane. In this way, it may be arranged that the reagents are delivered sequentially to the detection zone without the need for impermeable barriers or slow release agents.

Figure 9:
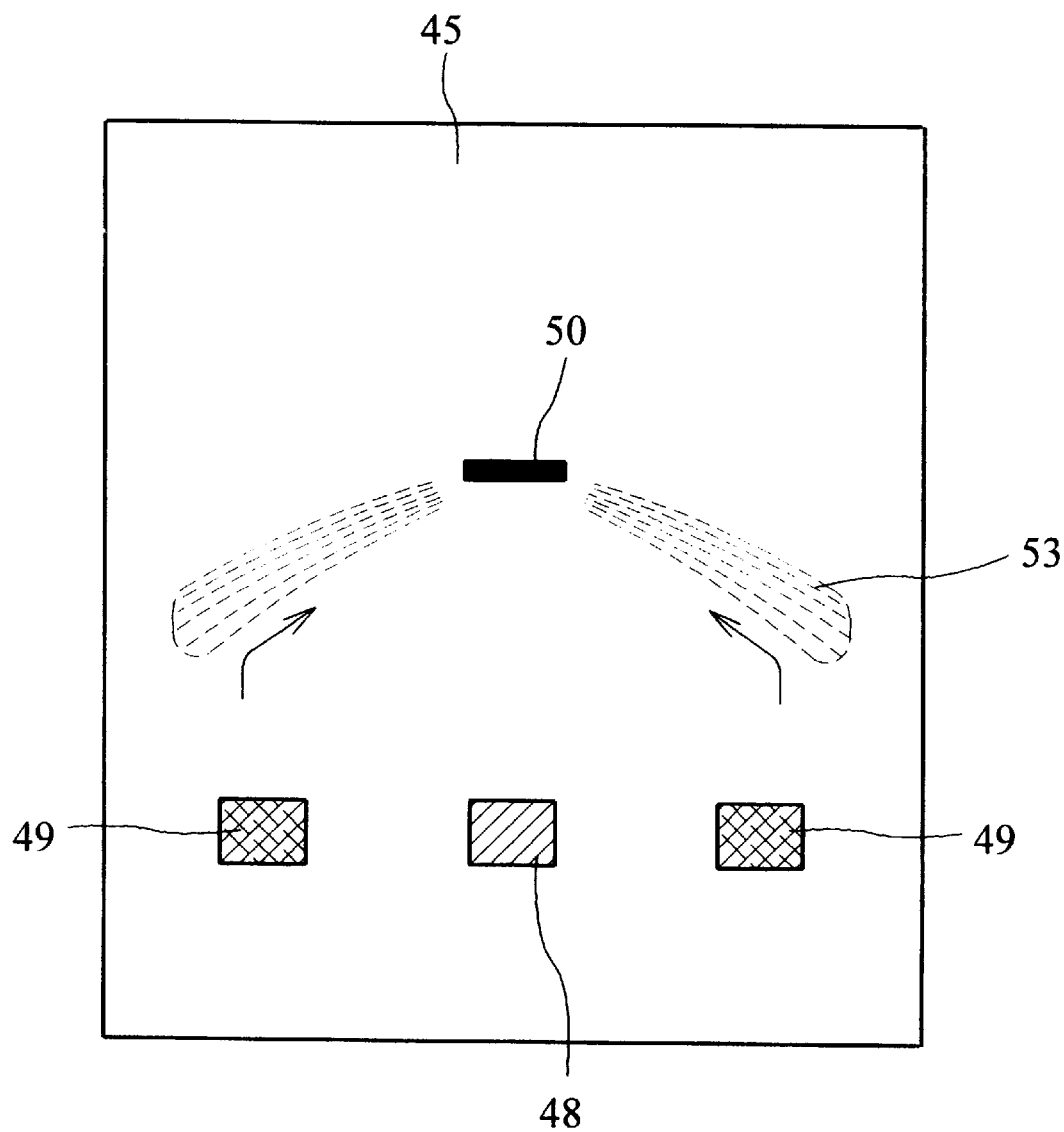
FIG. 9 is a schematic drawing illustating an analytical test device in which sequential delivery of reagents to a detection zone is achieved using an enhancement reaction to change liquid flow automatically during use.

One such embodiment is shown in FIG. 9. In this embodiment, the labelled reagent (48) is postioned on the carrier (45) such that it can proceed under laminar flow directly to the binding agent (50) in the detection zone. The enhancement reagent (49) is positioned such that if it proceeds under laminar flow, it will by-pass the detection zone. However gold particles (53) are deposited on the carrier in the path of the enhancement reagent (49) such that as the sample continues to flow along the carrier, a barrier forms in the path of the enhancement reagent (49) effectively diverting the flow into the detection zone as indicated by the arrows.

Figure 10:
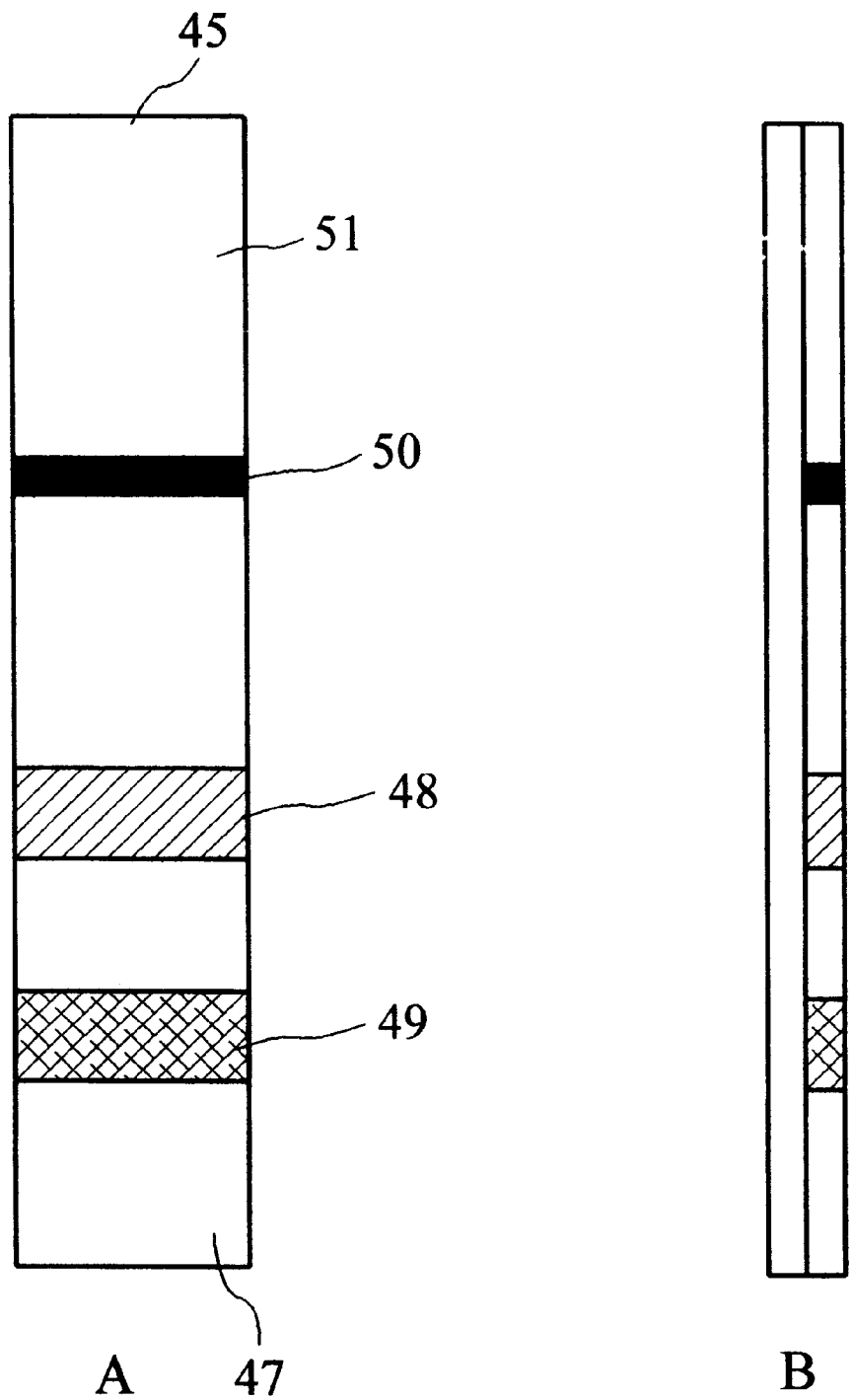

Alternatively the device may take the shape of a simple dipstick as shown in FIG. 10 where all reagents are deposited across the strip in different zones and their controlled release effected by the application of suitable release reagents at each zone. Thus the sample is applied to the lower edge (47) of the strip and flows through each zone drawn by capillary action towards the upper portion (51). The sample passes through the enhancing reagent (49) without causing immediate release and continues to the labelled binding protein (48) where an interaction takes place between the sample analyte and the labelled binding protein (48), at the same time releasing the labelled binding protein. The latter then moves towards the capture binding protein (50) with further interaction to form a sandwich as previously described if such specific analyte is present in the sample. Excess sample liquid passes through the capture zone to an upper region of the strip (51) which may have an overlapping wick or larger surface area (not shown) to draw the sample effectively through the detection zone.

Subsequent release of the enhancing reagent (49) occurs by continuous flow of the sample liquid, this release being controlled by the choice of slow release reagent as described above. The enhancing reagent (49) is likewise drawn through the detection zone causing the signal to become visible.

Any number of reagents may be deposited in this way on the lower portion of the membrane to allow any number of sequential reactions to occur. The use of small gold particular labels followed by silver enhancement, or enzyme labels followed by colour reaction substrates provides a greater indirect signal intensity than the direct signals given by larger gold or particular labels in the conventional rapid test systems presently available. In addition the method allows a wash step between reactions at the capture zone, the washing being provided by the sample itself. There may in addition be more than one capture binding reagent immobilised in the detection zone to allow simultaneous detection of more than one analyte from the sample.

Figure 11:
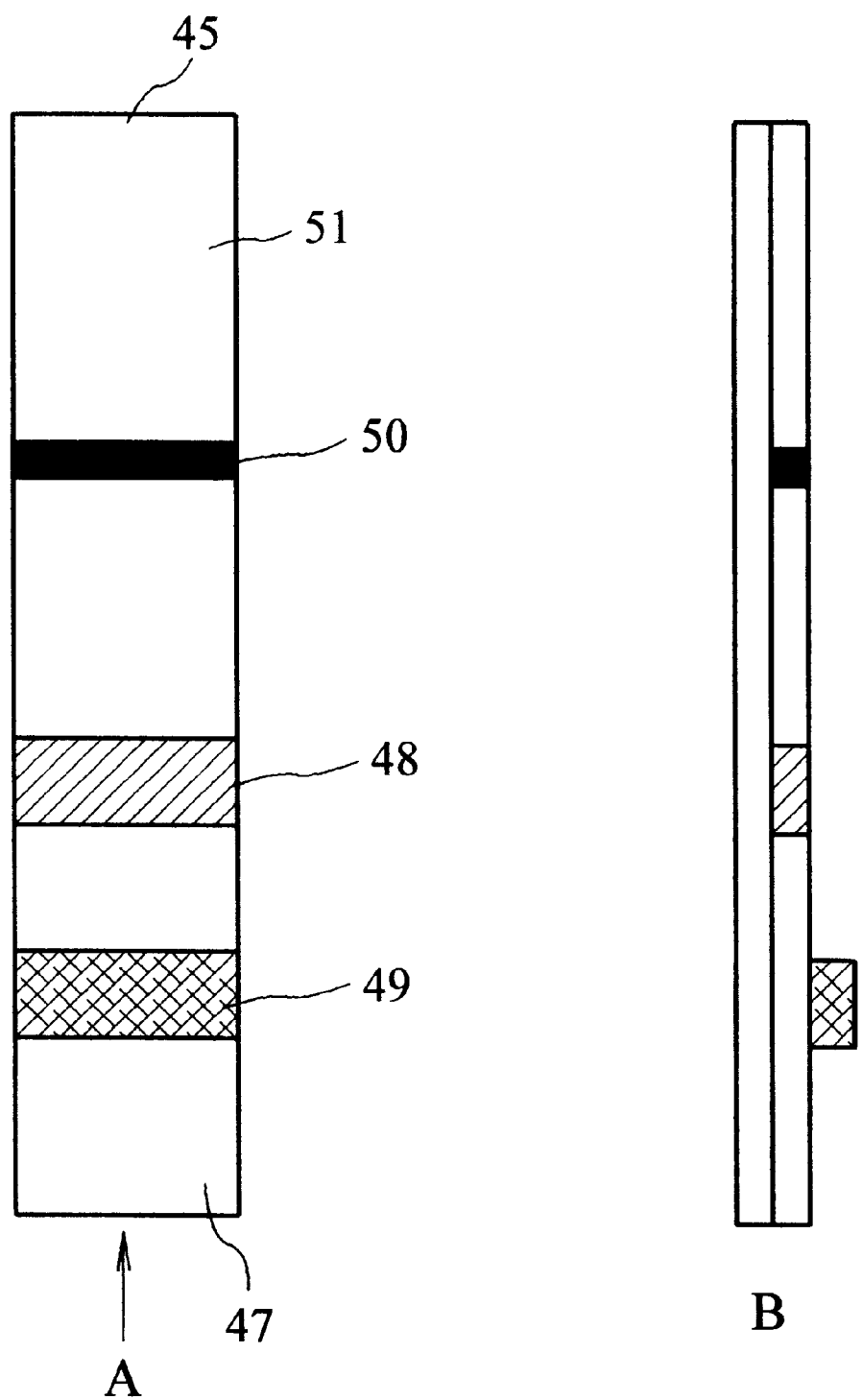

Alternatively the mobile labelled binding reagents and/or enhancing means may be deposited on separate layers of permeable membrane, paper or glass fibre etc which make contact on the surface of the device membrane so that the sample liquid moves first underneath this second layer towards the capture zone and, after a controlled time interval, through it, thus releasing the labelled binding reagent or label developing means. This is illustrated in FIG. 11 which shows an embodiment in which the enhancement reagent (49) is located on a glass fibre pad (54) fixed onto the surface of the carrier (45). The time interval before release of the labelled binding reagent or label developing means may be controlled by the choice of the material forming the second layer and by the choice of releasing agents within this second layer. The speed of movement of the reagents through the device membrane is controlled by prior treatment of the membrane or second layer material with a suitable blocking agent such as surfactant, polymer, protein, sugar, resin, etc, either alone or in combination.

In an extension of this principle, several layers of such membranes may be incorporated in one place, each carrying different reacting substances to be solubilised sequentially and transferred to the device membrane. These several layers may or may not be separated by uncoated membranes to allow a more precise sequential release onto the device membrane. One advantage of such a layered arrangement is that the labelled binding reagents and/or the label developing means are not initially incorporated within the body of the device membrane, thus allowing free flow of sample fluid to the capture zone.

Such a device may be used as described in a sandwich assay or, as previously described for the liquidic circuit design, in a competitive assay. In the competitive assay format, the second binding agent (50) competes with the sample analyte for binding to the first binding reagent (48). The first binding reagent (48) is moved into the detection zone under the influence of the liquid sample under test but in this instance, any which has bound to the sample analyte will not be retained in the detection zone. Only unbound first labelled binding reagent (48) will be accumulated there and subsequently give rise to the visible signal. In this instance the greater the signal the less analyte is present in the sample, indicative of a lack of analyte in the sample. The immediate labelled binding reagent (48) will be invisible at the detection zone but subsequent enhancement by the sequential arrival of the enhancing reagent (49) will render the label visible to a higher intensity than the conventional direct labels currently employed.

Devices of the invention may also be used for detection of specific antibodies in serum, saliva, or other body fluids or prepared sample liquids from other sources. A particularly suitable embodiment in this case is shown in FIG. 12. The form of the device is broadly similar to that shown in FIG. 7. However, in this case, the immobilised capture reagent (50a) may be an antigen specific to the antibody being detected. The labelled binding reagent (48) may be a suitable binding protein such as Protein A or Protein AG, or anti Human IgG, etc, labelled with small gold particles or other particulate material or enzymes, etc. The enhancing reagents (49) may again be silver enhancing reagents, enzyme substrates, or dyes, etc as previously described. The sequential release of these binding reagents allows timed reactions to occur at the detection zone.

The sample containing specific and non specific antibodies first moves through an unobstructed gap (55) to react directly with the immobilised antigen (50a) in the detection zone. Subsequent release of the labelled reagent (48) allows this to react with the sample antibody now immobilised at the detection zone. The controlled sequential release of the labelled binding reagent (48) and the enhancing reagent (49) is provided by similar release substances as described above or by being deposited behind or within semipermeable barriers as also described above. The sample continues to pass through the detection zone providing a wash step before the subsequently released enhancing reagent (49) provides a visible signal.

In order to decrease the attachment of non specific antibodies present in the sample to the labelled binding reagent (48) the latter may be partially shielded by a band of anti IgG (56). In this arrangement the sample passes through the band of anti IgG (56) to cause the release and flow of the labelled binding reagent (48) and subsequently of the enhancing reagent (49) but both the specific and non specific IgG are filtered out of this portion of the sample.

If required wicking zones may be provided both for application of the sample to the lower edge of the membrane and to the upper portion to allow satisfactory capillary draw of the sample through the detection zone. The device may be suitably shaped as shown in FIG. 12 to allow focusing of the sample and reagents through the diffusion means (52) and detection or capture zone.

Alternatively the device may take the form shown in FIG. 10 in which all reagents are deposited across the strip in different zones and their controlled release effected by application of suitable release materials at each zone. Thus the sample may be applied to the lower edge of the strip and flows through each zone drawn by capillary action towards the upper portion (51). In this case, the reagents are placed such that the sample may pass through the enhancing reagent (49) and the labelled binding reagent (48) without causing immediate release of either of these reagents. The sample passes towards the detection zone whereupon the sample analyte binds specifically to the capture reagent (50). Further flow of the sample liquid causes the subsequent release of labelled binding reagent (48) which then flows towards and through the capture zone, binding with the specific antibodies immobilised there from the sample. Further flow of sample liquid effects the subsequent release of enhancing reagents (49) which then flows to the capture zone to enhance the label and produce a visible signal.

Figure 13:
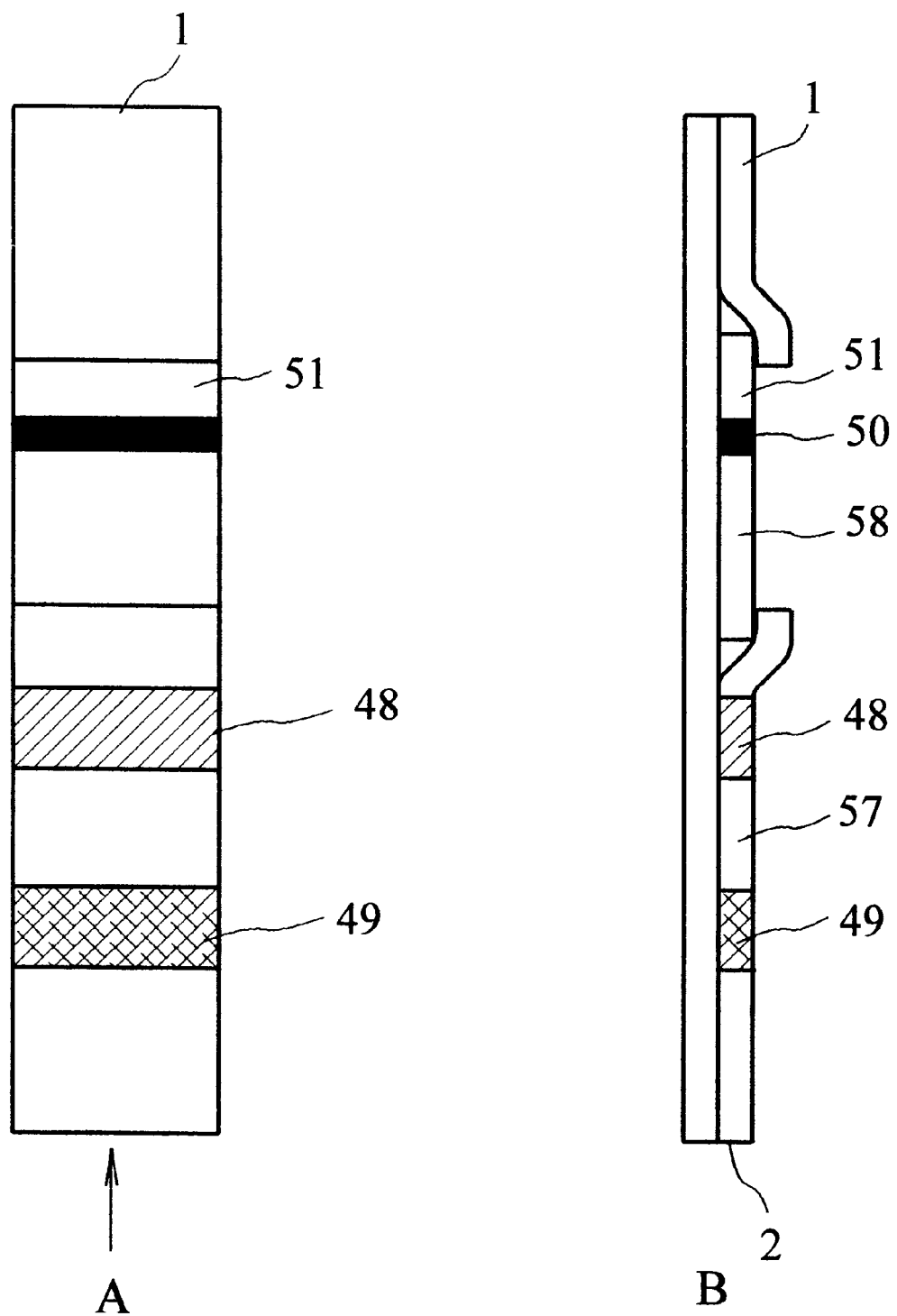

In a preferred embodiment, the device is in the form of a simple dipstick as shown in FIG. 13 where the mobile reagents (48, 49) are deposited in different zones on a lower pad or wick (57) comprising for example glass fibre, and contained within slow release materials such as guma arabic etc. as described above which control the release of the different reagents appropriately. Sample is applied to the lower edge (47) of the strip and flows through each reagent zone drawn by capilliary action towards the detection zone. The samples passes through the lower wick (57) without causing immediate release of the enhancing reagent (49) and continues to the labelled binding reagent (48) where an interaction takes place between the sample analyte and the labelled binding reagent (48), at the same time releasing the latter. The resultant liquid then transfers onto a membrane (58) and moves towards the binding reagent (50) with further interaction to form a sandwich as previously described if such specific analyte is present in the sample. Excess sample liquid passes through the detection zone to an upper region (51) which may be provided with an overlapping wick (59) or larger surface area to draw the sample effectively through the detection zone. Subsequent flow of the sample liquid causes the release and flow of enhancing reagent (49) from the lower wick so that they in turn transfer to the membrane and flow towards the detection zone where an enhancement of the label takes place. Further flow of the sample causes a wash of excess enhancing reagent from the target zone.

A similar but more simple arrangement, using slow release reagents for the labelled binding reagent may be made using a visible label in any of the embodiments shown in FIGS. 7 to 13 above without the need for a subsequent enhancement in order to visualise the signal.

The assay devices of the invention may be supplied complete or they may be supplied in kit form comprising which the porous element which includes for example, appropriate impermeable barriers and/or marks to indicate where the reagents may be added, or bands or antibodies etc. The appropriate reagents may or may not form part of the kit.

The following Examples are provided by way of illustration only.

EXAMPLE 1

A device substantially as shown in FIG. 10 was constructed as follows. Nitrocellulose membrane of 8 μm pore size and supported on a stiff plastic backing was obtained from Advanced Micro Devices, New Delhi, India. A strip of this membrane was cut 5 mm wide and 80 mm long. For the simple demonstration of the invention a stripe of rabbit IgG (Sigma Chemicals Ltd, Poole, UK) was diluted to 1 mg/ml in deionised water and applied across the strip 4 cm from the bottom edge at a strength of 1 μl/cm using a piezoelectric ink jet printer specially designed for printing proteins for diagnostic devices (Bioprinter, British Biocell International Ltd, Cardiff, UK). The protein stripe was dried at 37 C for 15 min. The strip was then blocked by immersion in a solution of 0.1% Tween 20 and 1% polyvinyl pyrrolidine (Sigma UK). The strip was dried at 37° C. for 30 min. Goat anti-rabbit IgG conjugated to 1 nm gold particles (British Biocell, UK) was diluted to an antibody concentration of 1 μg/ml in 0.1% Tween 20 and 1% polyvinyl pyrrolidine and 5 μl pipetted onto the strip approximately 3 cm from the bottom edge. A Light Microscope Silver Enhancing Kit, SELK15, (British Biocell International Ltd), comprising an initiator and a developer was obtained. Both the initiator and the developer were independently diluted 1:1 in an aqueous 1% solution of gum arabic (Sigma Chemicals, UK Ltd). 2μl of each reagent was pipetted onto the membrane strip, the initiator being 1 cm from the bottom edge and the enhancer being 2 cm from the bottom edge. The strip was dried at 37° C. for 30 min. The strip was then placed in a microwell containing 100 μl of phosphate buffered saline. The gold labelled goat anti rabbit IgG moved towards the immobilised rabbit IgG and was captured within one minute but without obvious signal. Within a further two minutes the initiator and the enhancer moved up the strip to the captured gold labelled antibody and produced an intense black signal.

EXAMPLE 2

A sandwich assay was produced for the detection of beta HCG in urine as illustrated in FIG. 10. A nitrocellulose membrane 8 μm pore size, (AMD, India) on a plastic backing, was striped with a 1 mg/ml solution of monoclonal anti alpha HCG (Sigma Chemicals Ltd, UK) at a concentration of 1 μl/cm in water with the Bioprinter. The strip was dried at 37° C. for 15 min. The membrane strip was blocked by immersion in a mixture of 0.1% Tween 20 and 1% polyvinyl pyrrolidine (Sigma Chemicals Ltd, UK) for 1 minute and then dried at 37° C. for 30 min. Monoclonal anti beta HCG conjugated to 1 nm gold particles (British Biocell, UK) was diluted to an antibody concentration of 1 μg/ml in 0.1% Tween 20 and 1% polyvinyl pyrrolidine and 5 μl pipetted onto the strip approximately 3 cm from the bottom edge.

Both enhancer and initiator were applied to the strip as above and the strip dried at 37° C. for 30 min. The strip was placed in a microwell containing 100 μl of urine from a 4 week pregnant female. The sample caused the movement of gold conjugate from the strip towards the capture zone while reacting with the sample beta HCG analyte. Within 3 minutes the sample caused the silver enhancing reagents to move from the membrane strip towards the capture zone to produce an intense black line indicating the presence of the analyte. Further flow of the sample caused the strip to be washed clean of any background staining.

EXAMPLE 3

A further sandwich assay was prepared for the detection of hepatitis B surface antigen in a standard sample in the form shown in FIG. 10. A nitrocellulose membrane 8 μm pore size, (AMD, India) on a plastic backing, was striped with a 1 mg/ml solution of monoclonal anti hepatitis surface antigen (Genzyme, UK) at a concentration of 1 μl/cm in water with the Bioprinter. The strip was dried at 37° C. for 15 min. The membrane strip was blocked by immersion in a mixture of 0.1% Tween 20 and 1% polyvinyl pyrrolidine (Sigma Chemicals Ltd, UK) for 1 minute and then dried at 37° C. for 30 min. A second monoclonal anti hepatitis B surface antigen conjugated to 1 nm gold particles (British Biocell, UK) was diluted to an antibody concentration of 1 μg/ml in 0.1% Tween 20 and 1% polyvinyl pyrrolidine and 5 μl pipetted onto the strip approximately 3 cm from the bottom edge. Both enhancer and initiator were applied to the strip as above and the strip dried at 37° C. for 30 min. The strip was placed in a microwell containing 100 μl of PBS spiked with a standard concentration of hepatitis B surface antigen (Genzyme UK). The sample caused the movement of gold conjugate from the strip towards the capture zone while reacting with the sample hepatitis analyte. Within 3 minutes the sample caused the silver enhancing reagents to move from the membrane strip toward the capture zone to produce an intense black line indicating the presence of the analyte.

EXAMPLE 4

According to the preferred embodiment of FIG. 13 a device was constructed as follows: Nitrocellulose membrane of 8 μm pore size and supported on a stiff plastic backing (Advanced Micro Devices, New Delhi, India) was cut 5 mm wide and 25 mm long. An upper paper wick was applied with a 2 mm overlap onto the membrane. The strip was striped with a 1 mg/ml solution of monoclonal anti alpha HCG (Sigma Chemicals Ltd, UK) at a concentration of 1 μl/cm in water with the Bioprinter at a distance of approximately 4 cm from the bottom edge. The strip was dried at 37° C. for 15 min. The membrane strip was blocked by immersion in a mixture of 0.1% Tween 20 and 1% polyvinyl pyrrolidine (Sigma Chemicals Ltd, UK) for 1 minute and then dried at 37° C. for 30 min. Monoclonal anti beta HCG conjugated to 1 nm gold particles (British Biocell, UK) was diluted to an antibody concentration of 1 μg/ml in 0.1% Tween 20 and 1% polyvinyl pyrrolidine and 5 μl pipetted onto a separate strip of glass fibre measuring 5×30 mm, approximately 2 cm from the bottom edge. Both enhancer and initiator from a Silver Enhancing Kit (SEKL15, British Biocell International Ltd, UK) were also applied to a separate strip of glass fibre (Whatman, UK), by pipetting 5 μl of each solution in separate areas at a distance of 5 mm from each other on the surface and dried at 37° C. for 15 min. The glass fibre strip was held in place by a layer of double sided adhesive tape on the plastic backing carrying the nitrocellulose membrane such that it overlapped the membrane by 1 mm. The assembled strip was placed with the lower end in a microwell containing 100 μl of urine from a 4 week pregnant female. The sample caused the movement of gold conjugate from the glass fibre strip towards the capture zone while reacting with the sample beta HCG analyte. Within 3 minutes the sample caused the silver enhancing reagents to move from the glass fibre strip onto the nitrocellulose membrane and upwards towards the capture zone to produce an intense black line indicating the presence of the analyte.

EXAMPLE 5

A device as shown in FIG. 7 was prepared using a strip of nitrocellulose 25 mm wide and 80 mm long (Advanced Micro Devices, India)which was printed with a boundary of insoluble ink using a marker pen as shown by the broken line of FIG. 7. This design did not create any separate channels for the reagents but allowed a funnelling of the reagents towards the detection zone. The strip was printed in the detection zone with a 1 mg/ml solution of monoclonal anti alpha HCG (Sigma Chemicals Ltd, UK) at a concentration of 1 μl/cm in water with the Bioprinter over the entire width of the channel and at a distance of approximately 4 cm from the bottom edge. The strip was dried at 37° C. for 15 min. The membrane strip was blocked by immersion in a mixture of 0.1% Tween 20 and 1% polyvinyl pyrrolidine (Sigma Chemicals Ltd, UK) for 1 minute and then dried at 37° C. for 30 min. Monoclonal anti beta HCG conjugated to 1 nm gold particles (British Biocell, UK) was diluted to an antibody concentration of 1 μg/ml in 0.1% Tween 20 and 1% polyvinyl pyrrolidine and 5 μl pipetted onto the strip in the region 48 in FIG. 7, approximately 1 cm from the bottom edge and just right of centre. Both enhancer and initiator from a Silver Enhancing Kit (SEKL15, British Biocell International Ltd, UK) were applied to the zone indicated by 49 by pipetting 3 μl of each, the two reagents being separated by approximately 5 mm, just left of centre, and the membrane dried at 37° C. for 15 min. The silver enhancing reagents were positioned approximately 2 cm from the bottom edge and just left of centre. The strip was placed with the lower end in a well containing 100 μl of urine from a 2 week pregnant female. The sample caused the movement of gold conjugate from the strip towards the capture zone while reacting with the sample beta HCG analyte. Within 3 minutes the sample caused the silver enhancing reagents to move from the glass fibre strip onto the nitrocellulose membrane and upwards towards the capture zone to produce an intense black line indicating the presence of the analyte. Further flow of the sample from the bottom edge provided a wash of the remaining reagents from the membrane into the upper zone.

The above-described devices allows a highly sensitive assay to be performed in a rapid manner using a one step procedure. Many different arrangements may be envisaged depending upon the assay being carried out, the reagents available and the sort of assay required and these form part of the invention.

What is claimed is:

1. An assay device for detecting whether or not an analyte is present in a sample, wherein a visible signal indicative of the presence or absence of said analyte is produced at a detection site on a support, wherein the device is a strip device having a single channel and said signal is generated or enhanced by means of a signal enhancement reaction between a first binding reagent which comprises an invisible label and a label developing means which is effective to render the invisible label visible, said first binding reagent and label developing means being arranged to be delivered to the detection site in a single assay step by application of the sample, but in a sequential manner such that the first binding reagent arrives at the detection site ahead of the label developing means.

2. An assay device comprising
   (a) a porous element;
   (b) a first binding reagent which specifically binds an analyte, is movable through the porous element under the influence of a liquid into a detection zone in a single step by application of the sample alone to the device, and comprises an invisible label;
   (c) a second binding reagent which specifically binds either said analyte in a manner which is complementary to that of the first binding reagent or which competes with said analyte for binding to said first binding reagent and is immobilised within said detection zone; and,
   (d) label developing means movable under the influence of a liquid into said detection zone after said first binding reagent, said label developing means being able to render the invisible label visible;
   wherein the device is a strip device having a single channel and the first binding reagent and the label developing means are arranged to be delivered to the detection zone in a single step by application of the sample.

3. The assay device of claim 2 wherein said invisible label comprises a particulate metal label and the label developing means comprises a reagent which deposits solid material on the surface of said metal.

4. The assay device of claim 3 wherein the size of the particles of the label is in the range of from 1 to 100 nm.

5. The assay device of claim 3 wherein the label is a particulate gold label.

6. The assay device of claim 5 wherein the label developing means comprises a silver containing reagent.

7. The assay device of claim 3, wherein the size of the particles of the label is less than 5 nm.

8. The assay device of claim 2 wherein said label developing means is applied to the porous element such that its release from the element in the presence of a liquid is delayed compared to the release of the first labelled binding reagent.

9. The assay device of claim 8 wherein the label developing means is applied in the form of a composition which comprises a slow release agent.

10. The assay device of claim 8 or claim 9 wherein the label developing means is contained within a second porous element which is in contact with the porous element.

11. The assay device of claim 10 wherein the second porous element is a glass fibre pad.

12. The assay device of claim 8 wherein the first binding reagent is applied in a composition which comprises a slow release agent.

13. The assay device of claim 2 wherein movement of the movable reagents from the porous element membrane is controlled by modifying the hydrophobicity of the porous element.

14. The assay device of claim 2 wherein movement of at least the label developing means through the porous element is inhibited by a semipermeable barrier.

15. The assay device of claim 3 wherein the label developing means is arranged to first contact label which is present on the porous element, such that deposition of material on said label creates a barrier which diverts liquid flow to the detection zone.

16. The assay device of claim 2 which further comprises a housing which is open to allow administration of sample and which allows the detection zone to be observed.

17. The assay device of claim 2 which comprises at least one wick or wicking region arranged to assist the passage of liquid through the device.

18. The assay device of claim 2 wherein diffusion means are provided such that reagents are evenly distributed prior to reaction in a detection zone.

19. The assay device of claim 2 which is arranged such that the detection zone is washed between reaction stages.

20. The assay device of claim 19 wherein liquid sample suspected of containing analyte is used as wash liquid.

21. The assay device of claim 20 which is provided with filter means to remove undesired elements from said wash liquid.

22. The assay device of claim 21 adapted for use as a serological assay, wherein the filter means comprises a anti-antibody, arranged so that it removes antibodies from the serum sample.

23. The assay device of claim 1 wherein the labelled first binding reagent comprises a labelled nucleic acid probe, and said analyte comprises a nucleic acid sequence which is immobilised in the detection zone.

24. A method for detecting the presence of an analyte in a liquid sample, which method comprises applying said liquid sample to an assay device of claim 1, and recording whether a visible signal appears.

25. The diagnostic assay device of claim 1 wherein a liquid is allowed to move through a porous element to produce a signal indicative of the presence or absence of an analyte, said device further comprising a first reagent and a second reagent which are arranged so that they react together in the course of the assay to produce a physical barrier which diverts liquid flow through the porous element.

26. The assay device of claim 1 wherein, a series of specific binding products are formed at a detection zone on a porous element, and wherein wash liquid is applied to said zone between the formation of at least two said specific binding products, and the wash liquid comprises part of the sample which has passed through filtration means provided on said element.

27. The assay device of claim 26 wherein the filtration means comprises a band of immobilised anti-antibody on the surface of the porous element positioned such that a portion of sample intended for use as a wash liquid passes through said filtration means prior to arrival at the detection site.

28. A method for performing a serological assay said method employing the assay device of claim 26, wherein the filtration means comprises a band of immobilized anti-body on the surface of the porous element positioned such that a portion of sample intended for use as a wash liquid passes through said filtration means prior to arrival at the detection site.

29. A kit comprising an assay device which is operable to carry out the method of claim 22.

* * * * *